United States Patent
Le Roy et al.

(10) Patent No.: US 9,463,338 B2
(45) Date of Patent: Oct. 11, 2016

(54) DERIVATIVES OF THE SINAPINIC ACID

(71) Applicant: PHARMASYNTHESE, Saint-Pierre-les-Elbeuf (FR)

(72) Inventors: Pierre-Yves Le Roy, Vert le Petit (FR); Yves Le Guen, Paris (FR)

(73) Assignee: PHARMASYNTHESE, Sainte-Pierre-les-Elbeuf (FR)

(*) Notice: Subject to any disclaimer, the term of this patent is extended or adjusted under 35 U.S.C. 154(b) by 0 days.

(21) Appl. No.: 14/759,773

(22) PCT Filed: Jan. 7, 2014

(86) PCT No.: PCT/FR2014/050017
§ 371 (c)(1),
(2) Date: Jul. 8, 2015

(87) PCT Pub. No.: WO2014/108629
PCT Pub. Date: Jul. 17, 2014

(65) Prior Publication Data
US 2015/0353469 A1 Dec. 10, 2015

(30) Foreign Application Priority Data
Jan. 8, 2013 (FR) ...................... 13 50125

(51) Int. Cl.
| | |
|---|---|
| C07D 309/40 | (2006.01) |
| A61Q 19/06 | (2006.01) |
| A61K 8/37 | (2006.01) |
| A61K 8/46 | (2006.01) |
| A61K 8/49 | (2006.01) |
| A61Q 19/02 | (2006.01) |
| A61Q 19/08 | (2006.01) |
| C07C 235/34 | (2006.01) |
| C07C 235/38 | (2006.01) |
| C07D 209/16 | (2006.01) |
| C07D 211/06 | (2006.01) |
| C07D 295/192 | (2006.01) |
| C07C 69/734 | (2006.01) |
| A61K 8/36 | (2006.01) |
| A61K 8/42 | (2006.01) |
| C07C 323/19 | (2006.01) |
| C07C 235/36 | (2006.01) |
| C07D 265/30 | (2006.01) |

(52) U.S. Cl.
CPC .............. *A61Q 19/06* (2013.01); *A61K 8/36* (2013.01); *A61K 8/37* (2013.01); *A61K 8/375* (2013.01); *A61K 8/42* (2013.01); *A61K 8/46* (2013.01); *A61K 8/49* (2013.01); *A61K 8/492* (2013.01); *A61K 8/498* (2013.01); *A61K 8/4926* (2013.01); *A61Q 19/02* (2013.01); *A61Q 19/08* (2013.01); *C07C 69/734* (2013.01); *C07C 235/34* (2013.01); *C07C 235/36* (2013.01); *C07C 235/38* (2013.01); *C07C 323/19* (2013.01); *C07D 209/16* (2013.01); *C07D 211/06* (2013.01); *C07D 265/30* (2013.01); *C07D 295/192* (2013.01); *C07D 309/40* (2013.01); *A61K 2800/78* (2013.01); *C07C 2101/02* (2013.01); *C07C 2101/14* (2013.01)

(58) Field of Classification Search
CPC .................................................... C07D 309/40
See application file for complete search history.

(56) References Cited

FOREIGN PATENT DOCUMENTS

| EP | 1437117 A1 | 7/2004 |
|---|---|---|
| EP | 1967175 A1 | 9/2008 |

OTHER PUBLICATIONS

Mar. 4, 2014 Search Report issued in International Patent Application No. PCT/FR2014/050017.

*Primary Examiner* — Shawquia Jackson
(74) *Attorney, Agent, or Firm* — Oliff PlC

(57) ABSTRACT

The object of the present invention is a compound of general formula (I)

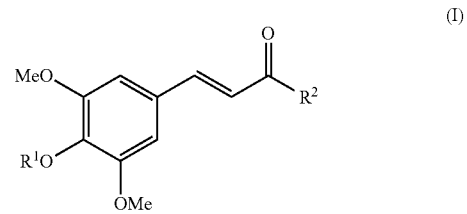

as well as to its pharmaceutically acceptable salt, and to the use of this compound for cosmetic and pharmaceutical applications.

13 Claims, No Drawings

DERIVATIVES OF THE SINAPINIC ACID

The present invention relates to new derivatives of the sinapinic acid and the use of these derivatives for cosmetic or pharmaceutical applications.

Antioxidants

Oxidation is a part of a redox reaction which transfers electrons from one substance to an oxidant agent. This reaction can produce free radicals that lead to chain reactions. Although the oxidation reactions are necessary for life, they may also be destructive.

The oxidative stress has been questioned in the pathogenesis of several human diseases. Thus, the oxidative stress can damage, and even kill cells and may be a partial cause of the development of several chronic degenerative diseases including cancer, cardiac dysfunction and neuronal degeneration. It is also known that oxidant molecules can damage biological molecules such as proteins, lipids or DNA. Although the human body has developed tools for fighting the free radicals, the elimination process is not 100% effective.

Nowadays, it is widely accepted that the oxidative stress is involved in the ageing process of the skin cell (Ames, B. N., Shigenaga, M. K. and Hagen, T. M. (1993), <<Oxidants, Antioxidants, and the Degenerative Diseases of Aging>>, *Proc. Natl. Acad. Sci. USA* 90, 7915-7922). Hence, the antioxidants are likely to delay skin ageing.

The antioxidants are capable of stopping these chain reactions by being reduced with the free radicals, thereby annihilating their action. Thus, plants and animals use and produce several antioxidants, that is to say molecules likely to decrease or prevent the oxidation of other chemical substances.

In the context of cosmetic treatment of skin ageing, it is therefore useful to identify compounds having an antioxidant activity.

Elastin

Elastin is a protein belonging to the family of structural-type fibrous proteins. Elastin is synthesized and secreted in the extracellular space by the fibroblasts, first into proelastin, then into tropoelastin.

Elastin is the major component of the elastic fibers.

Elastin is found in the dermis of the skin, the latter acting as a support. In particular, the proper operation of the skin is closely related to the characteristics of elastin which may be stretched up to 150% of its length at rest before breaking.

Thus, it enables the tissues to be stretched and to return to their initial state after stretching, which gives them flexibility.

Moreover, the total production of elastin stops around puberty, after which the available quantity of elastin will decrease over time which will result, for example during ageing, in a loss of elasticity and tonicity of the dermis which can no longer resist the effects of contraction of the underlying muscles, giving rise to the appearance of wrinkles.

In the context of cosmetic treatment of skin ageing, it is therefore useful to identify compounds capable of inducing a significant increase of elastin neo synthesis.

Collagen

Collagen is a family of proteins, most often present in fibrillar form. It is present in the extracellular matrix of the organisms. The function of these proteins is to confer the tissues with a mechanical resistance to stretching.

In contrast with elastin which is also present in the connective tissues, collagen is inextensible and resists traction quite well. Different types of collagen exist depending on the considered organ. For example, type I collagen (which represents 90% of collagen of a vertebrate) constitutes the frame of the bone (to be compared with the rebar of the reinforced concrete), and more generally of ordinary connective tissues. It is found in the bones, the skin, the tendons, the cornea and in the internal organs.

The production of collagen in the skin starts decreasing at the age of 25, but this slowdown accelerates at the age of forty, with a collagenous loss which may be around 1% per year.

As a result of the slowdown in the production of collagen and its alterations, the skin retains less water, becomes less flexible, gets thinner and wrinkles.

In the context of cosmetic treatment of skin ageing, it is therefore useful to identify compounds that promote the neo synthesis of type I collagen (pro-collagen I).

Progerin

The skin ageing may also be attributed to some well-known diseases, among which progeria or Hutchinson-Gilford syndrome. The symptoms of this disease are characterized by an accelerated ageing which leads to the death of the patient.

In this pathology, the lamin-A, a protein participating in the formation of the nuclear lamina and involved in the stability of the nucleus of the structure of chromatin and of the gene expression, is present in a truncated form, called progerin.

On the other hand, it has recently been shown (C. Verdy, J.-E. Branka and N. Mekideche, <<Quantitative assessment of lactate and progerine production in normal human cutaneous cells during normal ageing: effect of an *alaria esculenta* extract>>, *Int. J. Cosmetic Science,* 2011, 1-5) that extracts of the *Alaria esculenta* algae, inducing a significant decrease of the neo synthesis of progerin, also present a significant effect on a skin anti-ageing activity.

In the context of cosmetic treatment of skin ageing or therapeutic treatment of skin ageing, in particular of Hutchinson-Gilford syndrome, it is therefore useful to identify compounds that allow to decrease the neo synthesis of progerin.

Glycerol

The adipose tissue (fat mass) is a special connective tissue the constitution of which resembles the constitution of a connective tissue, with a ground substance, fibers and its cells. In fact, it is a connective tissue which contains fatty cells that store lipids, called <<adipocytes>>.

These lipid reserves are constituted by triglycerides. These triglycerides are synthesized inside the adipocyte but the endocytosis, that is to say the diffusion of these triglycerides through the cytoplasmic membrane, is not facilitated. Hence, the adipocyte will excrete in the blood a lipase in order to cleave the triglycerides into fatty acids and glycerol which can be easily assimilated by the adipocyte. The reverse mechanism is performed when excreting the lipid reserves by means of an enzyme, namely lecithin.

In the context of a slimming cosmetic treatment, it is therefore useful to identify compounds that allow decreasing the rate of glycerol in the adipose tissues.

Melano Modulators

The epidermis, the hair and the bristles are colored by pigments, the melanins, produced by specific large-sized cells: the melanocytes. They are located in the deepest layer of the epidermis. These melanin pigments serve to protect the epidermis and the deep layers of the sink from external attacks, in particular from UV rays. Thus, the melanins play an important photo-protective role. The biosynthesis of melanin is carried out according to a complex series of enzymatic reactions called melanogenesis.

In the context of a skin-whitening or skin-lightening cosmetic treatment, it is therefore useful to identify compounds that allow regulating (decreasing) the synthesis of melanin.

The sinapinic acid, also called sinapic acid or 3,5-dimethoxy-4-hydroxycinnamic acid, is a phenolic acid of chemical formula:

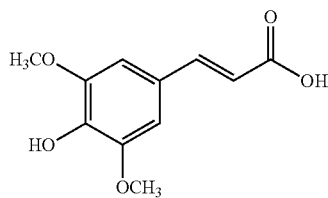

The sinapinic acid can be found in a wide variety of plants, in particular in the oilseed plants, in particular in the rapeseeds.

The use of the sinapinic acid and its close derivatives in the cosmetic field is known in the prior art. Thus, the patent application EP-A-1437117 describes the use of the sinapinic acid and its close derivatives for preparing cosmetic compositions likely to be used in the context of anti-ageing or anti-wrinkles treatment.

The patent application EP-A-1967175 describes on the other hand the use of derivatives of the sinapinic acid as a skin-whitening agent. An anti-ageing activity is also suggested. Nonetheless, no experimental result that allows confirming such an activity is provided.

Nonetheless, none of these patent applications describes the compounds according to the present invention.

However, new derivatives of the sinapinic acid have now been found which, quite surprisingly, are effective in the context of the cosmetic treatment of skin ageing; in the context of the therapeutic treatment of skin ageing, in particular in the context of the treatment of Hutchinson-Gilford disease; and/or in the context of a slimming cosmetic treatment.

Hence, the object of the present invention is a compound of general formula (I)

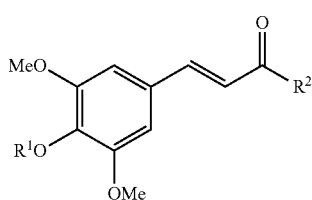

wherein:
R$^1$ is chosen as being a C$_2$-C$_6$-alkyl group or a —(C=O)—R$^3$ group;
R$^2$ is chosen as being a —O—R$^4$ or a —(N)R$^5$R$^6$ group;
R$^3$ is chosen as being a C$_1$-C$_6$-alkyl group;
—R$^4$ is chosen as being a C$_{12}$-C$_{16}$-alkyl group, a C$_{12}$-C$_{16}$-alkenyl group, a C$_{12}$-C$_{16}$-alkynyl group, a 4-pyranone group, a C$_1$-C$_{16}$-alkylphenyl group, a C$_2$-C$_{16}$-alkenylphenyl group, a C$_2$-C$_{16}$-alkynylphenyl group, a C$_3$-C$_6$-cycloalkyl group, a C$_1$-C$_{16}$-alkyl-C$_3$-C$_6$-cycloalkyl group, a C$_2$-C$_{16}$-alkenyl-C$_3$-C$_6$-cycloalkyl group and a C$_2$-C$_{16}$-alkynyl-C$_3$-C$_6$-cycloalkyl group;
each of these groups being optionally substituted with one or more substituent(s) chosen independently of each other as being a hydroxy group, an amine group, a C$_1$-C$_6$-alkyl group, a C$_1$-C$_6$-hydroxyalkyl group, a C$_1$-C$_6$-alkoxy group, a C$_1$-C$_6$-alkylthio group, a C$_1$-C$_6$-alkylcarbonyloxy group, a phenyl group, a C$_1$-C$_6$-alkoxyphenyl group, or a C$_2$-C$_6$-alkenylphenyl group optionally substituted with one or more substituent(s) chosen independently of each other as being a C$_1$-C$_6$-alkyl group, a C$_1$-C$_6$-hydroxyalkyl group, a C$_1$-C$_6$-alkoxy group, a C$_1$-C$_6$-thioalkyl group or a C$_1$-C$_6$-alkylcarbonyloxy group;
R$^5$ and R$^6$ are chosen independently of each other as being a hydrogen atom or a group selected among C$_1$-C$_{16}$-alkyl, C$_2$-C$_{16}$-alkenyl, C$_2$-C$_{16}$-alkynyl, phenyl, C$_1$-C$_{16}$-alkylphenyl, C$_2$-C$_{16}$-alkenylphenyl, C$_2$-C$_{16}$-alkynylphenyl, C$_1$-C$_{16}$-alkoxyindole, C$_3$-C$_6$-cycloalkyl, C$_1$-C$_{16}$-alkyl-C$_3$-C$_6$-cycloalkyl, C$_2$-C$_{16}$-alkenyl-C$_3$-C$_6$-cycloalkyl and C$_2$-C$_{16}$-alkynyl-C$_3$-C$_6$-cycloalkyl;
each of these groups being optionally substituted with one or more substituent(s) chosen independently of each other as being a hydroxy group, an amine group, a C$_1$-C$_6$-alkyl group, a C$_1$-C$_6$-hydroxyalkyl group, a C$_1$-C$_6$-alkoxy group, a C$_1$-C$_6$-thioalkyl group, a C$_1$-C$_6$-alkylcarbonyloxy group, a phenyl group, a C$_1$-C$_6$-alkoxyphenyl group, or a C$_2$-C$_6$-alkenylphenyl group optionally substituted with one or more substituent(s) chosen independently of each other as being a C$_1$-C$_6$-alkyl group, a C$_1$-C$_6$-hydroxyalkyl group, a C$_1$-C$_6$-alkoxy group, a C$_1$-C$_6$-thioalkyl group or a C$_1$-C$_6$-alkylcarbonyloxy group;
or, R$^5$ and R$^6$ form, with the nitrogen atom to which they are linked, a heterocycle selected among piperidine, morpholine, hexamethyleneimine or pyrrolidine, optionally substituted with one or more C$_1$-C$_6$-alkyl; with the exception of the following compounds:
4-acetoxy-3,5-dimethoxy-N-morpholino-cinnamamide;
4-acetoxy-3,5-dimethoxy-N-(2-methylmorpholino)-cinnamamide; and
4-acetoxy-3,5-dimethoxy-N-(3,4,5-trimethoxyphenyl)-cinnamamide.

The compounds according to the present invention have never been described before. These compounds possess an antioxidant activity, are capable of inducing a significant increase in the neo synthesis of elastin and/or promote the neo synthesis of type I collagen (pro-collagen I), thereby allowing for their use in the context of the cosmetic treatment of skin ageing.

These compounds also allow decreasing significantly the neo synthesis of progerin and therefore may be used in the context of the therapeutic treatment of skin ageing, in particular in the context of the treatment of Hutchinson-Gilford disease, or in the cosmetic treatment of skin ageing.

The compounds of the invention allow decreasing the rate of glycerol in the adipose tissues, and are therefore useful in the context of a slimming cosmetic treatment. Finally, the compounds of the invention allow regulating (decreasing) the synthesis of melanin and therefore may be used in the context of a skin-whitening cosmetic treatment.

In the context of the present invention:
<<C$_x$-C$_y$-alkyl>> means a saturated, linear or branched hydrocarbon chain, and including from x to y carbon atoms;

«$C_x$-$C_y$-alkenyl» means an unsaturated, linear or branched hydrocarbon chain, containing at least one double bond, and including from x to y carbon atoms;

«$C_x$-$C_y$-alkynyl» means an unsaturated, linear or branched hydrocarbon chain, containing at least one triple bond, and including from x to y carbon atoms;

«$C_x$-$C_y$-alkoxy» means a —O—($C_x$-$C_y$-alkyl) group;

«$C_x$-$C_y$-cycloalkyl» means a saturated hydrocarbon group which can be mono- or polycyclic, and including from x to y carbon atoms;

the terms «alkyl», «alkenyl», «alkynyl», «cycloalkyl», as defined above, keep the same definition when they integrate the name of a group such as for example alkylthio, hydroxyalkyl, alkylphenyl, alkylcarbonyloxy, etc.;

«heterocycle» means any cycle of 5 or 6 atoms, at least one of which is a nitrogen, a sulfur or an oxygen atom;

«skin ageing treatment» means any cosmetic or therapeutic treatment comprising topical application of one or more active ingredient(s) in view of making less visible and/or decreasing the external signs of skin aging such as wrinkles;

«slimming cosmetic treatment» means any cosmetic treatment comprising topical application of one or more active ingredient(s) in view of achieving a reduction of the volume of the hypodermic adipose tissue and/or a reduction of striae or of the «orange peel» appearance of the skin tissue;

«skin-whitening cosmetic treatment» means any cosmetic treatment comprising topical application of one or more active ingredient(s) in view of achieving a reduction in the synthesis of melanin, in particular the cosmetic treatment of ephelides (freckles), chloasma (brown spots on the face), and pigmentations due to senescence.

Preferably, the object of the present invention is a compound of general formula (I) as previously defined wherein the following characteristics are selected individually or in combination:

$R^1$ is chosen as being a —(C=O)—$R^3$ group;

$R^3$ is chosen as being a methyl, an ethyl, a propyl, a butyl, a pentyl or a hexyl group. Still preferably, $R^3$ is chosen as being a methyl group;

$R^4$ is chosen as being a $C_{12}$-$C_{16}$-alkyl group, a phenyl group, a 4-pyranone group, a $C_1$-$C_{16}$-alkylphenyl group, a $C_2$-$C_{16}$-alkenylphenyl group and a $C_3$-$C_6$-cycloalkyl group, each of these groups being optionally substituted with one or more substituent(s) chosen independently of each other as being a hydroxy group, an amine group, a $C_1$-$C_6$-alkyl group, a $C_1$-$C_6$-hydroxyalkyl group, a $C_1$-$C_6$-alkoxy group, a $C_1$-$C_6$-alkylthio group, a $C_1$-$C_6$-alkylcarbonyloxy group, a piperidine group, a morpholine group, a phenyl group, a $C_1$-$C_6$-alkoxyphenyl group, or a $C_2$-$C_6$-alkenylphenyl group optionally substituted with one or more $C_1$-$C_6$-alkylcarbonyloxy. Still preferably, $R^4$ is chosen as being a $C_{12}$-$C_{16}$-alkyl group, a 4-pyranone group optionally substituted with one or more substituent(s) chosen independently of each other as being a $C_1$-$C_6$-hydroxyalkyl group, a phenyl group optionally substituted with one or more substituent(s) chosen independently of each other as being $C_1$-$C_6$-alkyl or $C_1$-$C_6$-hydroxyalkyl, $C_1$-$C_{16}$-alkylphenyl optionally substituted with one or more substituent(s) chosen independently of each other as being $C_1$-$C_6$-alkoxy, $C_1$-$C_6$-alkylthio, $C_1$-$C_6$-alkylcarbonyloxy, $C_1$-$C_6$-alkoxyphenyl or $C_2$-$C_6$-alkenylphenyl which is in turn substituted with one or more $C_1$-$C_6$-alkylcarbonyloxy, $C_2$-$C_{16}$-alkenylphenyl; and $C_3$-$C_6$-cycloalkyl. Still preferably, $R^4$ is chosen as being the 4-pyranone, the 3,4,5-trimethoxy benzyl or a $C_{16}$-alkyl;

$R^5$ and $R^6$ are chosen independently of each other as being a hydrogen atom or a group selected among $C_1$-$C_{16}$-alkyl, $C_2$-$C_{16}$-alkenyl, phenyl, piperidine, morpholine, $C_1$-$C_{16}$-alkylphenyl, $C_1$-$C_{16}$-alkoxyindole and $C_3$-$C_6$-cycloalkyl, each of these groups being optionally substituted with one or more substituent(s) chosen independently of each other as being a hydroxy group, an amine group, a $C_1$-$C_6$-alkyl group, a $C_1$-$C_6$-hydroxyalkyl group, a $C_1$-$C_6$-alkoxy group, a $C_1$-$C_6$-thioalkyl group, a $C_1$-$C_6$-alkylcarbonyloxy group, a phenyl group, a $C_1$-$C_6$-alkoxyphenyl group, or a $C_2$-$C_6$-alkenylphenyl group optionally substituted with one or more substituent(s) chosen independently of each other as being a $C_1$-$C_6$-alkyl group, a $C_1$-$C_6$-hydroxyalkyl group, a $C_1$-$C_6$-alkoxy group, a $C_1$-$C_6$-thioalkyl group or a $C_1$-$C_6$-alkylcarbonyloxy group. Still preferably, $R^5$ and $R^6$ are chosen independently of each other as being a hydrogen atom or a group selected among $C_1$-$C_{16}$-alkyl, $C_2$-$C_{16}$-alkenyl, phenyl, piperidine, morpholine optionally substituted with one or more substituent(s) chosen independently of each other as being a hydroxy or a $C_1$-$C_6$-alkyl group; a $C_1$-$C_{16}$-alkylphenyl group optionally substituted with one or more substituent(s) chosen independently of each other as being a hydroxy or a $C_1$-$C_6$-alkoxy group, a $C_1$-$C_{16}$-alkoxyindole group; and a $C_3$-$C_6$-cycloalkyl group. Still preferably, $R^5$ is a hydrogen atom and $R^6$ is chosen as being a $C_{16}$-alkyl or the 4-hydroxyphenylethyl; and/or $R^5$ and $R^6$ form, with the nitrogen atom to which they are linked, a heterocycle selected among piperidine, morpholine, hexamethyleneimine or pyrrolidine, optionally substituted with one or more $C_1$-$C_6$-alkyl.

The compounds of formula (I) may be prepared by any method known and commonly used by those skilled in the art, in particular by analogy with the methods described in *Chemische Berichte,* 1952, 12, 1181.

As example, some compounds of formula (I) according to the present invention, wherein $R^4$ consists of a —O—$R^6$ group, may be prepared:

either by condensation of the chloride of the 4-acetoxy sinapinic acid (obtained for example according to Monatsh, Chem 41, 271 (1920)) with a $R^6$ group as previously defined in the presence of a tertiary amine such as triethylamine, pyridine or diisopropylethylamine, at a temperature ranging from 20° C. to 155° C., and preferably at 25° C.;

or by esterification of the sinapinic acid within toluene under reflux with sulfuric acid or methanesulfonic acid as a catalyst, then by acetylation of the ester at ambient temperature in pyridine with acetic anhydride;

according to the following reaction schemes:

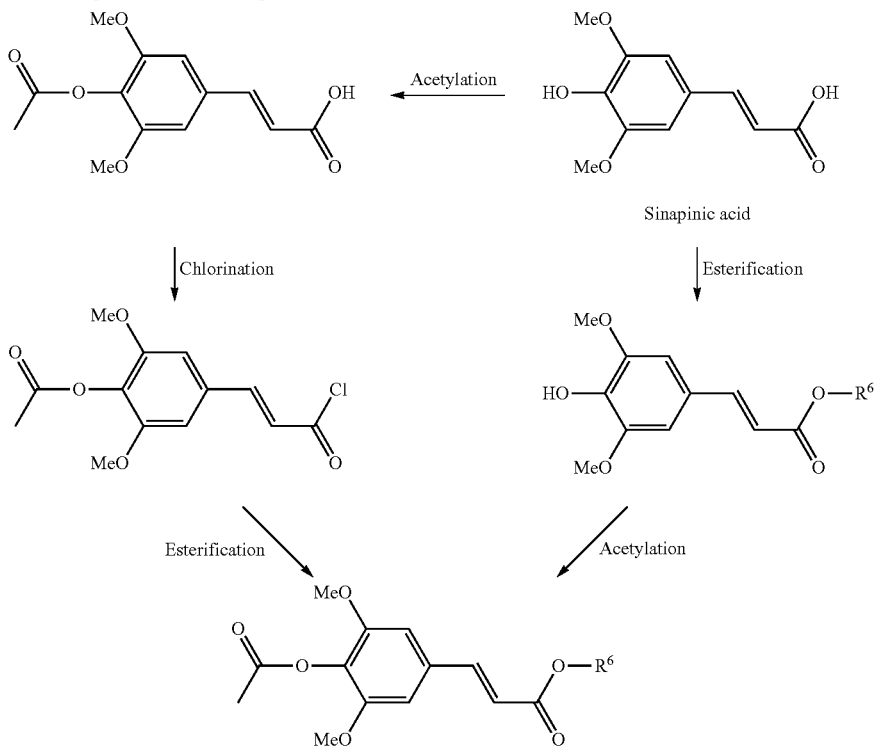

Similarly, some compounds of formula (I) according to the present invention, for which $R^4$ consists of a —(N)$R^7R^8$ group, may be prepared:
- either by condensation of the chloride of the 4-acetoxy sinapinic acid (obtained for example according to Späth, Monatsh, chem 41, 271 (1920)) with a —(N)$R^7R^8$ group, as previously defined, the reaction being carried out in a chlorinated solvent such as methylene chloride, chloroform or aromatic solvents such as toluene or dichlorobenzene, in the presence of a tertiary amine or a large excess of the reactive amine, at a temperature ranging from 20° C. to 155° C., and preferably at 25° C.;
- or by reaction, in dimethylformamide (DMF) or in tetrahydrofuran (THF), of the sinapinic acid acetate on an amine in the presence of EDCI and HOBt and a tertiary amine;
- or by a method called mixed anhydride method, that is to say, by reaction of the sinapinic acid acetate in acetone (or any other neutral solvent) with a tertiary amine such as triethylamine and an alkyl chloroformate such as ethyl chloroformate, or isobutyl chloroformate, followed by the reaction of a primary or a secondary amine;

according to the following reaction schemes:

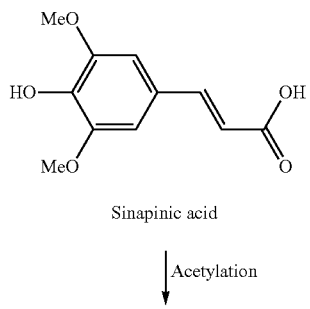

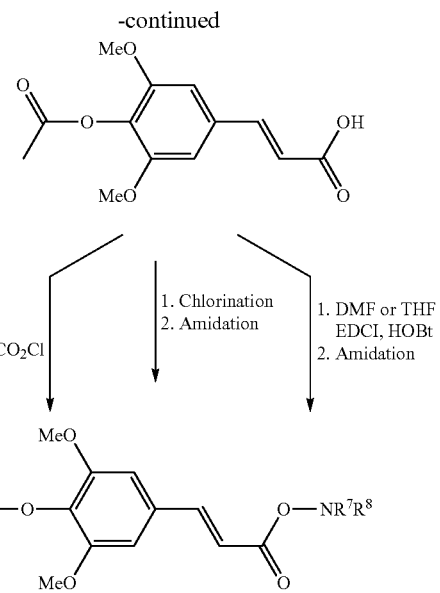

Hence, the compounds of formula (I) according to the present invention may be used in cosmetics for treatment of skin ageing, for a slimming treatment and/or for skin-whitening.

Hence, the present invention also relates to a cosmetic use of one or more compound(s) of formula (I) as previously defined, as anti-ageing agent(s), slimming agent(s) and/or skin-whitening agent(s).

The object of the present invention is also a cosmetic composition comprising (as an active ingredient) one or more compounds of formula (I) as previously defined, as well as its use for the cosmetic treatment of skin ageing, for a slimming cosmetic treatment and/or for a skin-whitening cosmetic treatment.

The compounds of formula (I) according to the present invention may also be used in the context of therapeutic treatment of skin ageing, in particular in the context of treatment of Hutchinson-Gilford disease.

Hence, the object of the present invention is also a pharmaceutical composition comprising (as an active ingredient) one or more compound(s) of formula (I) as previously defined. Preferably, the object of the present invention is a pharmaceutical composition comprising, as an active ingredient, one or more compound(s) of formula (I) as previously defined, for the treatment of skin ageing. Still preferably, the object of the present invention is a pharmaceutical composition comprising (as an active ingredient) one or more compound(s) of formula (I) as previously defined, for its use in the context of the treatment of Hutchinson-Gilford disease.

The cosmetic or pharmaceutical compositions according to the present invention may be formulated in any galenic form that is suitable for their administration. Thus, the compositions according to the present invention may be formulated in the form of cream, gel, lotion, milk, oil-in-water or water-in-oil emulsion, solution, ointment, spray, body oil, after-shave lotion, soap, lip protector stick, stick and makeup pencil.

The cosmetic or pharmaceutical compositions according to the present invention contain one or more compound(s) of formula (I) according to the present invention within contents ranging from 0.005% to 75% by total weight of the composition, preferably from 0.01% to 25% by total weight of the composition, still preferably from 0.05% to 5% by total weight of the composition.

For preparing these cosmetic or pharmaceutical compositions, one or more compound(s) of formula (I) according to the present invention or one or more of their pharmaceutically acceptable salt(s) are mixed with excipients that are commonly used in the cosmetic field.

The cosmetic or pharmaceutical compositions according to the present invention may be in the form of cream in which one or more compound(s) of formula (I) according to the present invention or one or more of their pharmaceutically acceptable salt(s) are associated with excipients that are commonly used in cosmetics.

The cosmetic or pharmaceutical compositions according to the present invention may be in the form of gels in the appropriate excipients such as cellulose esters or other gelling agents, such as carbopol, sepinov (polyacrylate), guar gum, etc.

The cosmetic or pharmaceutical compositions according to the present invention may also be in the form of lotion or solution in which one or more compound(s) of formula (I) according to the present invention or one or more of their pharmaceutically acceptable salt(s) are in an encapsulated form.

The microspheres in accordance with the invention may for example be constituted by fatty substances, agar and water. One or more compound(s) of formula (I) according to the present invention or one or more of their pharmaceutically acceptable salt(s) may be incorporated in vectors of the type liposomes, glycospheres, cyclodextrins, in chylomicrons, macro-, micro-, nanoparticles as well as macro-, micro- and nanocapsules and may also be absorbed on powdery organic polymers, talcs, bentonites and other mineral supports.

These emulsions have good stability and may be preserved as long as necessary for the use at temperatures comprised between 0 and 50° C. without sedimentation of the constituents or separation of the phases.

The cosmetic or pharmaceutical compositions according to the present invention may also contain additives or adjuvants that are commonly used in cosmetics, such as for example antimicrobial agents or perfumes but also extraction or synthesis lipids, gelling and viscosifying polymers, surfactants and emulsifiers, water-soluble or lipo-soluble active ingredients, plant extracts, tissue extracts, marine extracts, synthesis active ingredients.

The cosmetic or pharmaceutical compositions according to the present invention may also comprise other complementary active ingredients selected for their action. When the compositions according to the present invention contain complementary active ingredients, these are generally present in the composition at a concentration sufficiently high to enable them to exert their activity.

The cosmetic or pharmaceutical compositions according to the present invention are preferably used on a daily basis and applied once or several times a day.

The present invention is illustrated in a non-limiting manner by the following examples.

EXAMPLE 1

Compounds According to the Invention

| Compound | Melting point (° C.) | GC mass | LCHP mass |
|---|---|---|---|
| 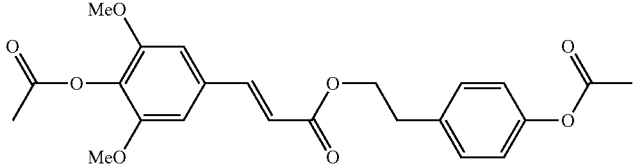 | | 132 | 428 |

Compound 1

-continued

| Compound | Melting point (° C.) | GC mass | LCHP mass |
|---|---|---|---|
| Compound 2 | 145 | | 386 |
| Compound 3 | 101 | | 370 |
| Compound 4 | 82 | | |
| Compound 5 | 158 | 446 | |
| Compound 6 | 134 | | 368 |
| Compound 7 | 132 | 446 | |

-continued

| Compound | Melting point (° C.) | GC mass | LCHP mass |
|---|---|---|---|
| Compound 8 | 143 | | 398 |
| Compound 9 | 142 | | 402 |
| Compound 10 | 183 | | 390 |
| Compound 11 | 208 | | 560 |
| Compound 12 | 112 | | |

-continued
| Compound | Melting point (° C.) | GC mass | LCHP mass |
|---|---|---|---|
| 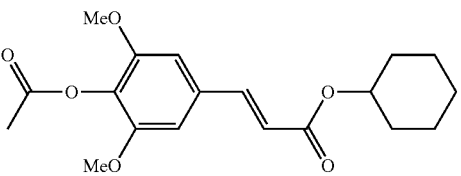Compound 13 | 137 | | |
| 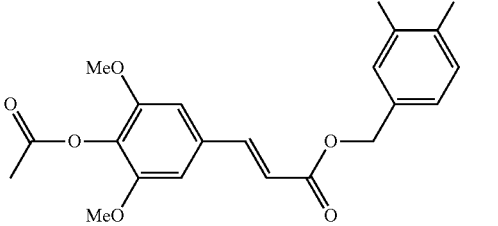Compound 14 | 118 | | 416 |
| 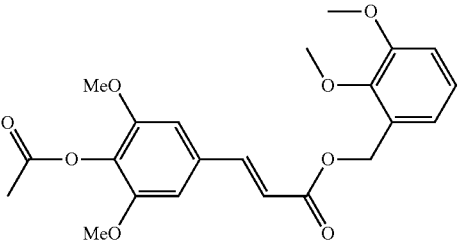Compound 15 | 143 | | 416 |
| 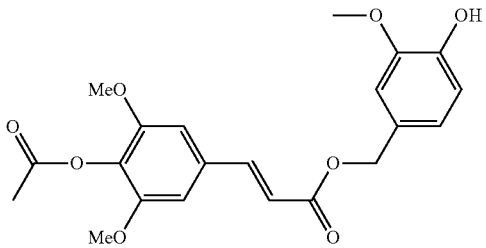Compound 16 | 191 | | 402 |

| Compound | Melting point (° C.) | GC mass | LCHP mass |
|---|---|---|---|
| 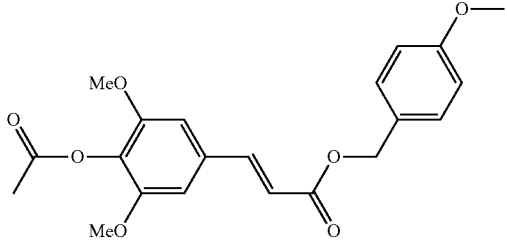<br>Compound 17 | 121 | | 386 |
| 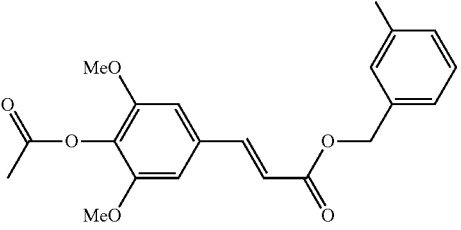<br>Compound 18 | 99 | | 386 |
| 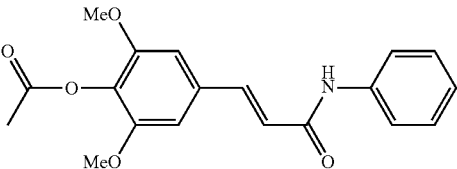<br>Compound 19 | 100 | | 341 |
| 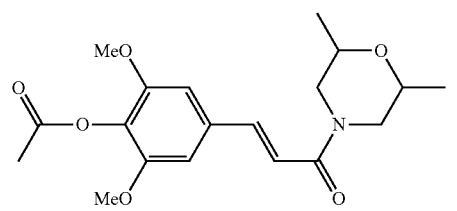<br>Compound 20 | 183 | | 363 |
| 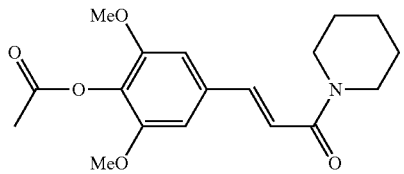<br>Compound 21 | 148 | | 333 |

-continued
| Compound | Melting point (° C.) | GC mass | LCHP mass |
|---|---|---|---|
| 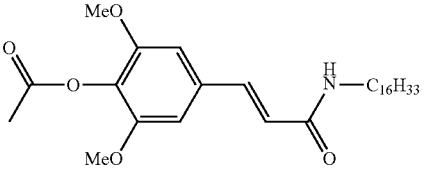 Compound 22 | 128 | | |
| 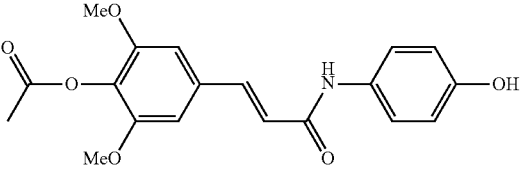 Compound 23 | 140 | | 357 |
| 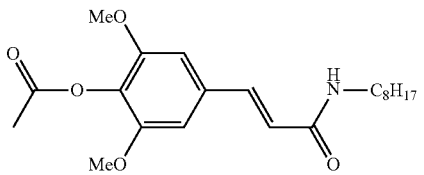 Compound 24 | 125 | | 377 |
| 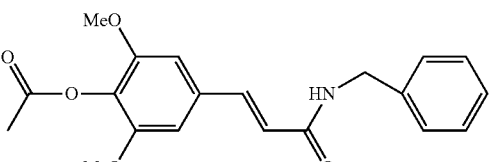 Compound 25 | 130 | | 355 |
| 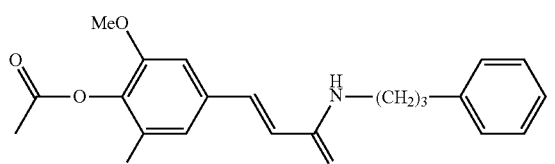 Compound 26 | 132 | | 383 |
| 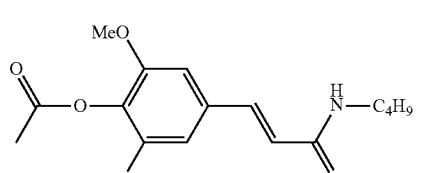 Compound 27 | 161 | | 321 |

-continued

| Compound | Melting point (° C.) | GC mass | LCHP mass |
|---|---|---|---|
| Compound 28 (3,5-dimethoxy-4-acetoxy cinnamoyl-NH-C₃H₇) | 143 | | 307 |
| Compound 29 (3,5-dimethoxy-4-acetoxy cinnamoyl-NH-(CH₂)₂-phenyl) | 137 | | 369 |
| Compound 30 (3,5-dimethoxy-4-acetoxy cinnamoyl-N(Me)-C₈H₁₇) | oil | | 391 |
| Compound 31 (3,5-dimethoxy-4-acetoxy cinnamoyl-NH-(CH₂)₂-(5-methoxyindol-3-yl)) | 148 | | 438 |
| Compound 32 (3,5-dimethoxy-4-acetoxy cinnamoyl-N(Me)-C₄H₉) | oil | | 335 |

-continued
| Compound | Melting point (° C.) | GC mass | LCHP mass |
|---|---|---|---|
| 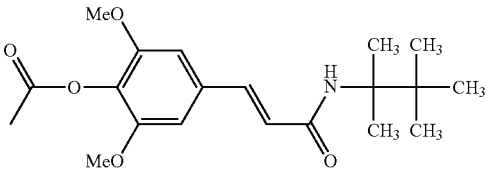  Compound 33 | 150 | | 377 |
| 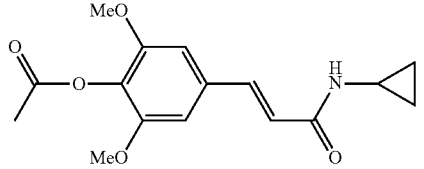  Compound 34 | 204 | | 305 |
| 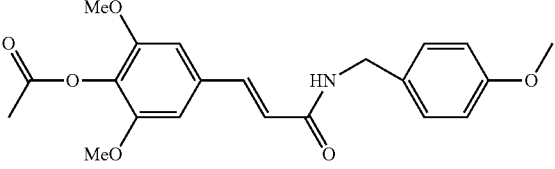  Compound 35 | 146 | | 385 |
| 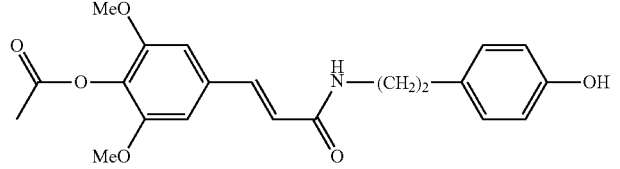  Compound 36 | 99 | | 385 |
| 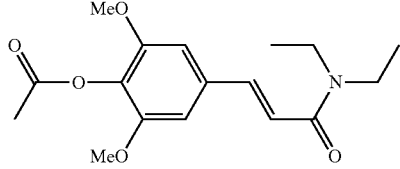  Compound 37 | 135 | | 321 |
| 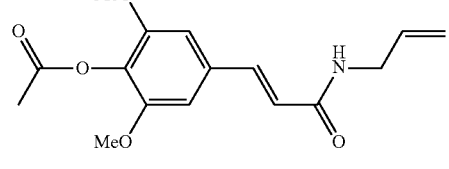  Compound 38 | 154 | | 305 |

-continued

| Compound | Melting point (° C.) | GC mass | LCHP mass |
|---|---|---|---|
| 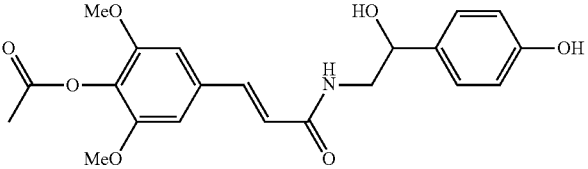 Compound 39 | | 204 | |
| 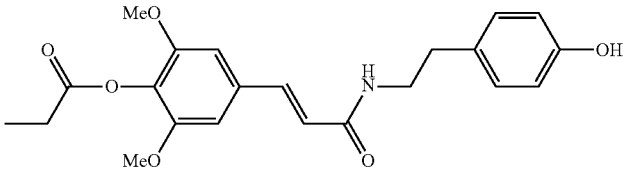 Compound 40 | | 399 | |
| 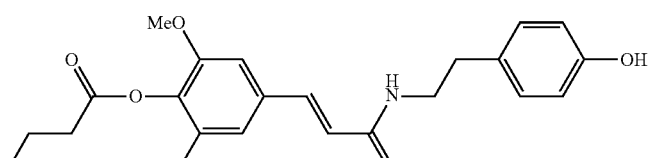 Compound 41 | | 413 | |

EXAMPLE 2

Preparation of the 4-acetoxy-3,5-dimethoxy cinnamate of 2-(4-acetoxyphenyl)-ethyl (Compound 1)

EXAMPLE 2.1

Preparation of the Sinapinic Acid Acetate Chloride

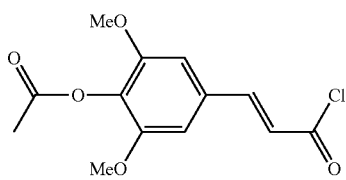 [SMILES: COc1cc(/C=C/C(=O)Cl)cc(OC)c1OC(C)=O]

7 g of sinapinic acid acetate are slurried in 60 ml of chloroform. 0.5 g of dimethylformamide (DMF) are added and then 9.4 g of thionyl chloride are poured. The mixture is stirred from 5 to 20 h at 20° C., and then heated under reflux from at least 3 hours to at most 8 hours.

The chloroform and the excess of thionyl chloride are distilled under vacuum at 50-60° C.

The sinapinic acid acetate chloride (melting point:140-144° C.) is obtained in the form of yellow crystallized product.

EXAMPLE 2.2

Preparation of the 4-acetoxy-3,5-dimethoxy cinnamate of 2-(4-acetoxyphenyl)-ethyl (Compound 1)

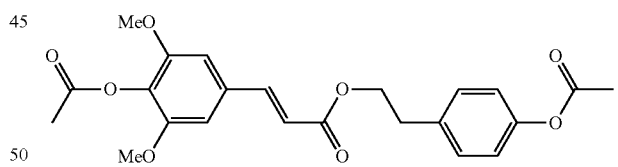

7.5 g of sinapinic acid acetate chloride obtained beforehand are placed in solution in 60 ml of chloroform or methylene chloride or toluene. 6 g of triethylamine (or any other tertiary amine) and then 7.2 g (1 mol. eq.) of 2-(4-hydroxyphenyl)ethyl acetate (obtained according to Tetrahedron, 56, (2000), 5169-5175) are added.

The mixture is stirred at 20° C. for 10 h. The progress of the reaction is monitored by TLC (chloroform/methanol 9/1, UV revelation). The solution is washed three times with 100 g of water, then concentrated to dryness under vacuum. The obtained crystals are recrystallized three times in 60 ml of absolute ethanol.

After filtering and drying, 2.4 g (yield of 43%) of 4-acetoxy-3,5-dimethoxy cinnamate of 2-(4-acetoxyphenyl)- ethyl (compound 1) in the form of an off-white powder which are isolated (melting point:132° C./GC/mass=98%) are obtained.

EXAMPLE 3

Preparation of the 4-acetoxy-3,5-dimethoxy cinnamate of 2-isopropyl-5-methyl phenyl (Compound 8)

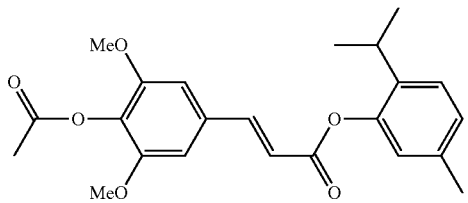 [SMILES: COc1cc(/C=C/C(=O)Oc2cc(C)ccc2C(C)C)cc(OC)c1OC(C)=O]

7.5 g of sinapinic acid acetate chloride obtained according to the example 2.1 are placed in solution in 60 ml of chloroform. 8 g of pyridine and 4 g of thymol are added.

The mixture is stirred at 20° C. for at least 10 h. The progress of the reaction is monitored by TLC (chloroform/methanol 9/1, UV revelation). The mixture is washed three times with 100 g of water. The organic phase is concentrated to dryness under vacuum. The obtained residue is recrystallized in the absolute ethanol.

After filtering and drying, 4.8 g (yield of 46%) of 4-acetoxy-3,5-dimethoxy cinnamate of 2-isopropyl-5-methyl phenyl in the form of a cream-colored powder (melting point: 143° C./GC/mass=98.5%), are obtained.

EXAMPLE 4

Preparation of the 4-acetoxy-3,5-dimethoxy cinnamate of n-hexadecyl (Compound 4)

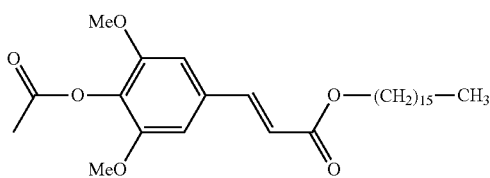

7.5 g of sinapinic acid acetate chloride, obtained according to the example 2.1, are placed in solution in 60 ml of dichloromethane. 8 g of diethylisopropylamine and 7 g of n-hexadecanol are added.

The mixture is stirred at 20° C. for about 20 h. The progress of the reaction is monitored by TLC (chloroform/methanol 9/1, UV revelation). The mixture is washed three times with 100 g of water. The organic phase is concentrated to dryness under vacuum. The obtained residue is recrystallized in the isopropanol.

After filtering and drying (at 60° C.), 6.0 g (yield of 44%) of 4-acetoxy-3,5-dimethoxy cinnamate of n-hexadecyl in the form of a white-cream powder (melting point:82° C./centesimal analyzes+/−0.3% compliant/NMR:compliant), are obtained.

EXAMPLE 5

Preparation of the 4-acetoxy-3,5-dimethoxy cinnamate of n-hexadecyl (Compound 4)

EXAMPLE 5.1

Preparation of the 3,5-dimethoxy cinnamate of n-hexadecyl

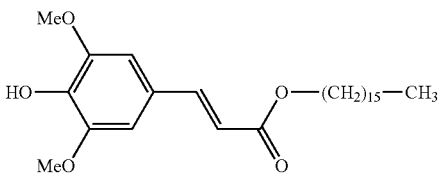

In a reactor equipped with a Dean-Stark apparatus, 11.2 g of sinapinic acid (I) are slurried in 100 ml of toluene. 20 g of n-hexadecanol and 1 g of sulfuric acid are added. The whole is refluxed for 5 h, the water is extracted.

The medium is cooled to 50° C. and concentrated under vacuum. 120 ml of ethyl acetate are added to the residue.

The solution obtained is washed twice with 100 g of water, then the solvent is concentrated under vacuum at 50° C. 120 ml of heptane are added to the residue and the whole is heated under reflux (solubilization) then cooled to 20° C.

The beige crystals are drained and dried at 60° C. 20 g (89% of yield) of 3,5-dimethoxy cinnamate of n-hexadecyl are isolated (melting point:62° C./FTIR:compliant/LCHP: 98.8%/NMR:compliant).

EXAMPLE 5.2

Preparation of the 4-acetoxy-3,5-dimethoxy cinnamate of n-hexadecyl (Compound 4)

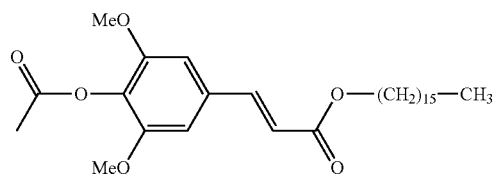

20 g of 3,5-dimethoxy cinnamate of n-hexadecyl, obtained beforehand, are dissolved in 100 g of pyridine and 28 g of acetic anhydride are added. The progress of the reaction is monitored by TLC in the chloroform/methanol (9/1) mixture.

After about 20 hours at 20° C., the solution is concentrated under vacuum at 55° C. 100 ml of methylene chloride are added to the residue and the solution obtained is washed twice with 100 g of water.

The organic phase is concentrated under vacuum. 110 ml of isopropanol are added to the residue and the whole is heated under reflux (solubilization) then cooled to 20° C. The crystals formed are drained and dried at 60° C. 12.8 g (57.3% of yield) of 4-acetoxy-3,5-dimethoxy cinnamate of n-hexadecyl in the form of a white powder are isolated (melting point:82° C./FTIR:compliant/NMR:compliant).

EXAMPLE 6

Preparation of the 4-acetoxy-3,5-dimethoxy-N-(phenyl)-cinnamamide (Compound 19)

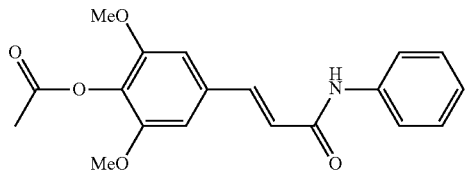

5 g of sinapinic acid acetate are placed in solution in 30 ml of dimethylformamide (DMF).

4 g of EDCI.HCl then 2.8 g of HOBt.H$_2$O are added. The medium is stirred at 20-25° C. for one hour.

10 g of triethylamine then 2 g of aniline are successively added to the medium. The mixture is stirred at 20° C. for 20 h. 100 g of water and 100 ml of chloroform are added, the medium is stirred for 30 minutes then left to decant.

The lower organic phase is extracted then washed twice with 70 ml of water and is concentrated to dryness under vacuum. The oily residue is taken up in 50 ml of heptane. The precipitate formed is filtered and dried in a ventilated oven at 60° C.

3.2 g (50% of yield) of 4-acetoxy-3,5-dimethoxy-N-(phenyl)-cinnamamide in the form of an off-white powder are isolated (melting point:100° C./LCHP mass:341/FTIR: compliant).

EXAMPLE 7

Preparation of the 4-acetoxy-3,5-dimethoxy-N-(cis-2,6-dimethylmorpholino)-cinnamamide (Compound 20)

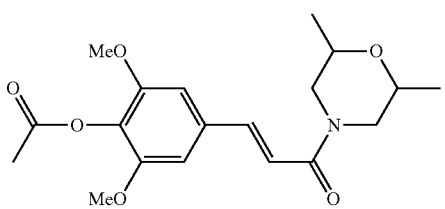 [SMILES: COc1cc(/C=C/C(=O)N2CC(C)OC(C)C2)cc(OC)c1OC(C)=O]

7.5 g of sinapinic acid acetate, obtained according to the example 2.1, are placed in solution in 60 ml of chloroform then the mixture is cooled to −10° C. 6 g of triethylamine then 3 g of cis-2,6-dimethylmorpholine are added dropwise at a temperature lower than 0° C.

The whole is stirred at 20° C. for 20 h. The reaction medium is washed 3 times with 100 g of water. The lower organic phase is concentrated to dryness under vacuum. The residue is recrystallized in isopropyl acetate. The precipitate formed is filtered and dried in a ventilated oven at 60° C.

5.2 g (54% of yield) of 4-acetoxy-3,5-dimethoxy-N-(cis-2,6-dimethylmorpholino)-cinnamamide in the form of a cream-colored powder are isolated (melting point:183° C./LCHP mass:363/FTIR:compliant).

EXAMPLE 8

Preparation of the 4-acetoxy-3,5-dimethoxy-N-(piperidino)-cinnamamide (Compound 21)

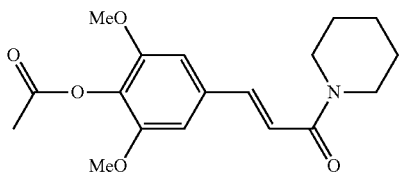 [SMILES: COc1cc(/C=C/C(=O)N2CCCCC2)cc(OC)c1OC(C)=O]

5 g of sinapinic acid acetate are slurried in 50 ml of acetone. 1.9 g of triethylamine are added. A solution is then obtained.

The whole is cooled to −10° C. and 2.6 g of isobutyl chloroformate are added dropwise at a temperature lower than −5° C. The whole is stirred for one hour between −5 and −10° C. then 1.7 g of piperidine are added, the temperature not exceeding 5° C. The medium is stirred at 20° C. for 20 h. 200 g of water are then added and the precipitate formed is filtered then dried in a ventilated oven at 60° C.

The solid obtained is recrystallized in a minimum of methanol. After filtering and drying, 3.5 g (55.5% of yield) of 4-acetoxy-3,5-dimethoxy-N-(piperidino)-cinnamamide in the form of a white powder are isolated (melting point: 148° C./LCHP mass:333/FTIR:compliant).

EXAMPLE 9

Preparation of the 4-acetoxy-3,5-dimethoxy-N-(3-phenylpropyl)-cinnamamide (Compound 26)

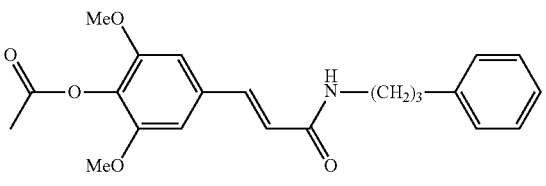

5 g of sinapinic acid acetate are slurried in 50 ml of acetone. 1.9 g of triethylamine are added.

The mixture is cooled to −10° C. and 2.4 g of ethyl chloroformate are added dropwise at a temperature lower than −5° C.

The whole is stirred for one hour between −5 and −10° C. then 2.55 g of phenyl-3-propylamine-1 are added, the temperature not exceeding 0° C. The mixture is stirred at 20° C. for 12 h.

50 g of water are then added and the precipitate formed is filtered and recrystallized in a minimum of ethanol at 96°. After filtering and drying, 4.6 g (62% of yield) of 4-acetoxy-3,5-dimethoxy-N-(3-phenylpropyl)-cinnamamide in the form of a white powder are isolated (melting point:132° C./LCHP mass:383/FTIR:compliant).

EXAMPLE 10

Preparation of the 4-acetoxy-3,5-dimethoxy-N-(5-methoxytryptamyl)-cinnamamide (Compound 31)

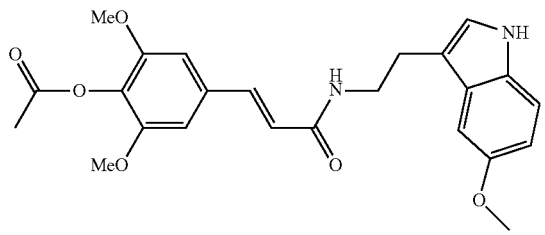 [SMILES: COc1ccc2[nH]cc(CCNC(=O)/C=C/c3cc(OC)c(OC(C)=O)c(OC)c3)c2c1]

5 g of sinapinic acid acetate are slurried in 100 ml of acetone. 1.7 g of triethylamineare are added.

The whole is cooled to −10° C. and 2.9 g of isobutyl chloroformate are added dropwise at a temperature lower than −5° C.

The whole is stirred for one hour between −5 and −10° C. and 3.6 g of 5-methoxytryptamine are then added, the temperature not exceeding 0° C. The medium is stirred at 25° C. for 48 h. 300 g of water are added.

After two hours of stirring, the precipitate formed is filtered then recrystallized in isopropanol. After filtering and drying, 4.2 g (51% of yield) of 4-acetoxy-3,5-dimethoxy-N-(5-methoxytryptamyl)-cinnamamide in the form of a cream-colored powder are isolated (melting point:148° C./LCHP mass:438/LCHP:98% s/s % FTIR:compliant).

EXAMPLE 11

Preparation of the 4-acetoxy-3,5-dimethoxy-N-(4'-hydroxyphenylethyl)-cinnamamide (Compound 36)

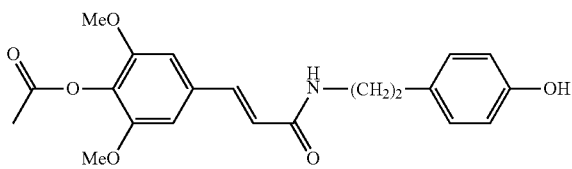

5 g of sinapinic acid acetate are slurried in 80 ml of acetone. 2 g of diisopropylethylamine are added.

The whole is cooled to −10° C. and 2.9 g of isobutyl chloroformate are added dropwise at a temperature lower than −5° C. The whole is stirred for one hour between −5 and −10° C.

2 g of diisopropylethylamine and 3.3 g of tyramine hydrochloride are then added. The medium is stirred at 20° C. for 24 h. 300 g of water are added.

After two hours of stirring, the precipitate formed is filtered then recrystallized in ethanol at 96°. After filtering and drying, 6.1 g (84% of yield) of 4-acetoxy-3,5-dimethoxy-N-(4'-hydroxyphenylethyl)-cinnamamide in the form of a slightly colored powder are isolated (melting point:99° C./LCHP mass:385/LCHP:98.1% s/s % FTIR:compliant).

EXAMPLE 12

Antioxidant Activity

The ORAC (Oxygen Radical Absorbance Capacity) method, described in Cao, G., Alessio, H. M., Cutler, R. G. Free radical Biology & Medecine 1993, 14: 303-311<<Oxygen-Radical Absorbance Capacity assay for antioxydants>> and Benderitter, M., Vincent-Genid, L., Pouget, J. P., Voisin, P. Radiation Research 2003; 159 (4): 471-483 <<The cell membrane as a biosensor of oxydative stress induced by radiation exposure:multiparameter investigation>>, has been used for measuring the anti-oxidant capability of the compounds of the invention.

By convention, the ORAC antioxidant activity of any molecule is measured in comparison with a recognized reference which is an analog of vitamin E, the trolox (6-hydroxy-2,5,7,8-tetramethylchroman-2-carboxylic acid), the anti-oxidant capability of 1 µM (micro mole) of trolox corresponding to 1 ORAC unit.

The ORAC values are commonly reported in µmol TE/g (in micromole of Trolox Equivalent per gram of product to be tested).

Given these definitions, the trolox has an ORAC index of about 3995 units.

The ORAC values of the compounds 26 and 34 have been measured (average of 3 measurements).

The results are reported in the following Table 1.

TABLE 1

| Compound | ORAC Antioxidant activity (µmol TE/g) |
| --- | --- |
| Trolox | 3995 |
| Compound 31 | 4874 ± 216 |
| Compound 39 | 20968 ± 992 |

Thus, it is observed that the compound 26 has an antioxidant activity which is slightly higher than the activity of the trolox, while the compound 34 has an antioxidant activity which is 5 times higher than that of the trolox.

EXAMPLE 13

Slimming Effects

The activity of the compounds of the invention on the adipocytes has been assessed. To do so, tests have been carried out on explants of adipose tissues that are kept alive according to the following experimental protocol.

The products to be tested are introduced in the culture medium. After 9 days of treatment, the activity is assessed through an assay of the glycerol released in the culture medium.

In order to be able to compare the potential activity of the molecules, caffeine (Sigma ref C-0750 batch 127F0396), which is known for its activity on the adipocytes (Studlar M. Z Ernahrungswiss. 1973 June; 12(2): 109-20, <<The effect of caffeine on the metabolism of lipids and carbohydrates>>), is used as a reference active ingredient.

The explants are prepared from a tummy tuck (P921-AB-40) carried out on a 40-year-old female donor. 54 explants of tissues have been prepared and kept alive in a medium which is supplemented with penicillin/streptomycin antibiotics (Gibco ref 15140 batch 918578) at 37° C. and with 5% of CO2.

The treatment has been carried out, on 3 explants, by incorporating 100 µl of the product (which is in turn at a 2% concentration in the adequate solvent, DMSO) in 2 ml of the culture medium on days J0, J2, J3, J5 and J7. Caffeine has been diluted to the desired concentration in the culture medium on these same days. The control explants have undergone no treatment.

On J0, the 3 explants have been collected and frozen at −80° C. On J9, the remaining explants have been collected and preserved under the same conditions. The extraction of lipids from the culture medium has been carried out according to a tested procedure. The assay of the glycerol of the culture medium has been carried out using a glycerol assay kit (Megazyme, K-GROL) in the form of 96-well microplates and reading has been made at 340 nm with a Tecam Infinite M200 microplate reader associated to the Magellan software.

The results obtained are reported in the following Table 2.

TABLE 2

| Glycerol (mg/ml) | Average | Standard deviation | % in comparison with caffeine |
|---|---|---|---|
| Culture medium | 0.022 | 0.005 | 4% |
| Caffeine (reference) | 0.096 | 0.022 | 100% |
| Compound 5 | 0.083 | 0.037 | 82% |
| Compound 22 | 0.114 | 0.047 | 124% |

Hence, the compounds 5 and 22 have an enhanced slimming activity in comparison with that of caffeine, recognized as being the reference in the field. In particular, the molecule 22 has a slimming action which is 24% higher than that of caffeine.

EXAMPLE 14

Effect on the Production of Progerin in Monolayer Cultures of Normal Human Dermal Fibroblasts Collected from a Mature Subject In order to study the influence of the compounds of the invention on the concentration of progerin in the cells, the assay method described by C. Verdy, J.-E. Branka and N. Mekideche in <<Quantitative assessment of lactate and progerine production in normal human cutaneous cells during normal ageing: effect of an *alaria esculenta* extract>>, *Int. J. Cosmetic Science*, 2011, 1-5, has been used.

The test system consists of monolayers of adult normal human dermal fibroblasts obtained by cultivating cells collected from a tummy tuck carried out on a 54-year-old woman.

Insulin at 10 nM has been used as a reference product in this study.

The cells have been incubated for 96 hours in the absence (control) or in the presence of the reference product or of increasing concentrations of the active ingredient that is being tested (0.01 µg/ml; 0.1 µg/ml; 1 µg/ml).

The compound to be tested is solubilized in 1 mg/ml in DMSO, then diluted in the cells incubation medium, with a constant concentration of 0.1% (v/v) in DMSO.

Upon completion of the incubation period, on the one hand, the progerin has been quantified in the cellular lysates (obtained by ultrasonic action) through a sensitive and specific ELISA assay, and on the other hand, the proteins that are contained in the cellular lysates have been quantified by a spectrophotometric method (Bradford method—Bradford M. (1976) Anal. Biochem., 72, 248-254).

The statistical significance of the differences that have been observed between the <<Control>> and the <<reference product>> conditions, has been assessed through a Student test. The statistical significance of the differences that have been observed between the <<Check>> and the <<test products>> conditions, has been assessed through a one-way analysis of variance (One Way ANOVA) followed by a Holm-Sidak test (*:$p<0.05$).

The results obtained are reported in the following Tables 3 and 4.

TABLE 3

| | Compound 2 (ng/ml) | | | Compound 5 (ng/ml) | | | Compound 10 (ng/ml) | | |
|---|---|---|---|---|---|---|---|---|---|
| | 10 | 100 | 500 | 10 | 100 | 500 | 50 | 500 | 5000 |
| Progerin | 233.7 | 170.6 | 300.1 | 284.0 | 206.0 | 916.2 | 274.9 | 301.7 | 261.2 |
| (ng/mg of | 353.5 | 196.3 | 328.4 | 243.7 | 364.1 | 1021.7 | 225.1 | 296.1 | 245.9 |
| protein) | 273.6 | 402.4 | 250.5 | 391.4 | 398.6 | 657.0 | 292.3 | 271.0 | 366.9 |
| Average | 286.4* | 256.4* | 293* | 306.4* | 322.9* | 865.0 | 264.1* | 289.6* | 291.4* |
| S.D. | 61.0 | 127.0 | 39.4 | 76.3 | 102.7 | 187.7 | 34.9 | 16.3 | 65.9 |
| % DMSO | 25.8 | 23.1 | 26.4 | 27.6 | 29.1 | 77.9 | 23.8 | 26.1 | 26.2 |
| Difference (%) | −74.2 | −76.9 | −73.6 | −72.4 | −70.9 | −22.1 | −76.2 | −73.9 | −73.8 |

*Average significantly indifferent from that of the DMSO group ($p < 0.05$)

TABLE 4

| | Compound 22 (ng/ml) | | | Compound 36 (ng/ml) | | |
|---|---|---|---|---|---|---|
| | 10 | 100 | 500 | 50 | 500 | 5000 |
| Progerin | 880.7 | 711.0 | 967.8 | 1552.2 | 249.8 | 215.8 |
| (ng/mg of | 801.5 | 548.8 | 727.4 | 690.1 | 288.8 | 200.8 |
| protein) | 830.7 | 500.9 | 562.4 | 555.6 | 252.1 | 207.9 |
| Average | 837.7 | 586.9* | 752.5 | 932.6 | 263.6* | 208.2* |
| S.D. | 40.1 | 110.1 | 203.9 | 540.8 | 21.8 | 7.5 |
| % DMSO | 75.4 | 52.9 | 67.8 | 84.0 | 23.7 | 18.8 |
| Difference (%) | −24.6 | −47.1 | −32.2 | −16.0 | −76.3 | −81.2 |

*Average significantly indifferent from that of the DMSO group ($p < 0.05$)

Under the retained experimental conditions, the compounds 2, 5, 10, 22 and 36 significantly decrease the neo synthesis of progerin and therefore counterbalance the disequilibrium in the production of progerin which is observed during ageing.

EXAMPLE 15

Effect on the Production of Type I Pro-Collagen in Monolayer Cultures of Normal Human Dermal Fibroblasts Collected from a Mature Subject The test system consists of monolayers of adult normal human dermal fibroblasts obtained by cultivating cells collected from a tummy tuck carried out on a 54-year-old woman.

The used reference activator is the Transforming Growth Factor $\beta$ (TGF-$\beta$) at 1 ng/ml. The cells have been incubated for 48 hours in the absence (control) or in the presence of the reference product or of increasing concentrations of the active ingredient that is being tested (10 ng/ml; 100 ng/ml; 500 ng/ml or 1000 ng/ml).

The compound to be tested is solubilized in 1 mg/ml in DMSO, then diluted in the cells incubation medium, with a constant concentration of 0.1% (v/v) in DMSO.

Upon completion of the incubation period, the type I pro-collagen contained in the fibroblasts incubation media has been quantified using a sensitive and specific E.I.A. kit.

Upon completion of the incubation period, the proteins contained in the cellular lysates have been quantified by a spectrophotometric method (Bradford method—Bradford M. (1976) Anal. Biochem., 72, 248-254).

The statistical significance of the differences that have been observed between the <<Control>> and the <<reference product>> conditions, has been assessed through a Student test. The statistical significance of the differences that have been observed between the <<Check>> and the <<test products>> conditions, has been assessed through a one-way analysis of variance (One Way ANOVA) followed by a Holm-Sidak test (*:p<0.05).

The results are given in the form of μg of type I pro-collagen per mg of protein (average+/− the standard deviation, S.D.) and are reported in the following Table 5.

TABLE 5

|  | Compound 5 (ng/ml) | | | Compound 10 (ng/ml) | | | Compound 36 (ng/ml) | | |
| --- | --- | --- | --- | --- | --- | --- | --- | --- | --- |
|  | 10 | 100 | 500 | 10 | 100 | 500 | 50 | 500 | 5000 |
| Procollagen | 45.3 | 53.0 | 66.1 | 45.6 | 74.0 | 90.6 | 68.1 | 59.2 | 73.8 |
| (pg/mg of protein) | 37.0 | 52.3 | 62.3 | 48.7 | 75.9 | 95.4 | 57.8 | 65.1 | 64.8 |
|  | 36.8 | 46.3 | 71.4 | 70.3 | 86.4 | 89.8 | 65.3 | 67.2 | 64.4 |
| Average | 39.7* | 50.5 | 66.6* | 54.9 | 78.8* | 91.9* | 63.7* | 63.9* | 67.7* |
| S.D. | 4.8 | 3.7 | 4.5 | 13.4 | 6.7 | 3.1 | 5.3 | 4.1 | 5.3 |
| % DMSO | 75.7 | 96.3 | 126.9 | 104.6 | 150.2 | 175.3 | 121.5 | 121.8 | 129.0 |
| Difference (%) | −24.3 | −3.7 | 26.9 | 4.6 | 50.2 | 75.3 | 21.5 | 21.8 | 29.0 |

*Average significantly indifferent from that of the DMSO group (p < 0.05)

The compounds given as examples induce a significant increase of the neo synthesis of type I pro-collagen, conferring them with an restructuring activity of the extracellular matrix, and therefore a skin anti-ageing effect

EXAMPLE 16

Effect on the Neo Synthesis of Elastin in Monolayer Cultures of Normal Human Dermal Fibroblasts Collected from a Mature Subject The test system consists of monolayers of adult normal human dermal fibroblasts obtained by cultivating cells collected from a tummy tuck carried out on a 54-year-old woman.

The used reference activator is the ascorbic acid at 100 μg/ml.

The cells have been incubated for 96 hours in the absence (control) or in the presence of the reference product or of increasing concentrations of the active ingredient that is being tested (10 ng/ml; 100 ng/ml; 500 ng/ml).

The compound to be tested is solubilized in 1 mg/ml in DMSO, then diluted in the cells incubation medium, with a constant concentration of 0.1% (v/v) in DMSO.

Upon completion of the incubation period, the elastin contained in the incubation medium of the explants has been quantified by a spectrophotometric method.

Upon completion of the incubation period, the proteins contained in the cellular lysate have been quantified by a spectrophotometric method (Bradford method—Bradford M. (1976) Anal. Biochem., 72, 248-254).

The results are given in the form of μg of elastin per mg of protein (average+/− the standard deviation, S.D.).

At a concentration of 10 ng/ml, the compounds 22 and 36 have resulted respectively in an increase of the neo synthesis of elastin of +16.7% and +63.7%.

EXAMPLE 17

Effect on the Synthesis of Melanin

These experiments allowed to show the capability of the compounds of the invention to modulate the melanin production of normal human melanocytes cultivated in D.K.K. fibroblast monolayers.

Test System

Monolayers of normal human dermal fibroblasts have been obtained by cultivating cells collected from a tummy tuck carried out on a 54-year-old woman. For carrying out the tests, these cells have been cultivated until obtaining confluent monolayers. Monolayers of normal human melanocytes have been obtained by cultivating cells collected from a tummy tuck carried out on a 41-year-old woman. For carrying out the tests, these cells have been cultivated until obtaining non-confluent monolayers.

Incubation of the Products

The fibroblasts have been incubated for 48 hours at 37° C. in a humid atmosphere with 5% of $CO_2$, in the absence (culture medium alone) or in the presence of increasing concentrations (10; 50 ng/ml) in compound 5.

Afterwards, the melanocytes have been incubated for 72 hours at 37° C. in a humid atmosphere with 5% of $CO_2$, in the absence (culture medium alone) or in the presence of kojic acid at 250 μM or of conditioned fibroblast media (see above) diluted to 1/10th in the culture medium of the melanocytes.

Preparation of the Active Ingredient Compound 5:

The active ingredient has been solubilized in DMSO (Dimethyl Sulfoxide). Afterwards, the dilutions have been carried out in the cells incubation medium with a constant concentration of 0.01% (v/v) of DMSO.

Assessment of the Effects

Melanin Assay

Upon completion of the incubation period, the intracellular melanin content has been quantified in the melanocytic lysates by a spectrophotometric measurement at 405 nm.

Proteins Assay

Upon completion of the incubation period, the proteins contained in the cellular lysates have been quantified by a spectrophotometric method (Bradford method).

Results & Statistics

The results are given in the form of μg of intracellular melanin per mg of total proteins of the cellular layer (averages+/− the standard deviation, S.D.).

The statistical significance of the differences observed between the <<Control>> and the <<test product>> conditions, has been assessed through a one-way analysis of variance (One Way ANOVA) followed by a Holm-Sidak test (*:p<0.05).

The results obtained are reported in the following Tables 6 and 7.

TABLE 6

|  | Check | Kojic acid 250 μM | DMSO 0.1% |
|---|---|---|---|
| Melanin/ | 16.7 | 14.3 | 15.8 |
| Proteins | 15.2 | 13.4 | 17.0 |
| (μg/mg) | 16.5 | 14.1 | 18.1 |
| Average | 16.1 | 14.0 | 17.0 |
| S.D. | 0.8 | 0.5 | 1.1 |
| % control | 100.0 | 86.6* | 105.1 |

*Average significantly indifferent from that of the DMSO 0.1% (p < 0.05)

TABLE 7

|  | Compound 5 | | | DMSO |
|---|---|---|---|---|
|  | 10 ng/ml | 50 ng/ml | 100 ng/ml | 0.01% |
| Melanin/ | 14.2 | 14.3 | 15.8 | 16.1 |
| Proteins | 11.7 | 14.7 | 16.7 | 17.3 |
| (μg/mg) | 13.7 | 14.7 | 16.0 | 18.4 |
| Average | 14.3* | 14.4* | 16.2 | 17.3 |
| S.D. | 1.3 | 0.2 | 0.5 | 1.1 |
| % DMSO | 83.0 | 83.6 | 93.7 | 100.0 |
| Difference (%) | −17.0 | −16.4 | −6.3 |  |

*Average significantly indifferent from that of the DMSO 0.1% (p < 0.05)

These results show that the compound 5 significantly decrease the synthesis of melanin in the melanocytes, conferring it with a bleaching activity.

The invention claimed is:

1. A compound of general formula (I)

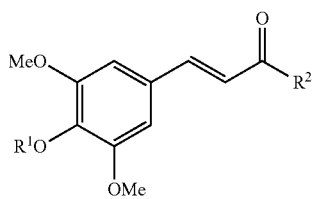

(I)

wherein:
$R^1$ is chosen as being a $C_2$-$C_6$-alkyl group or a —(C=O)—$R^3$ group;
$R^2$ is chosen as being a —O—$R^4$ or a —(N)$R^5R^6$ group;
$R^3$ is chosen as being a $C_1$-$C_6$-alkyl group;
$R^4$ is chosen as being a $C_{12}$-$C_{16}$-alkyl group, a $C_{12}$-$C_{16}$-alkenyl group, a $C_{12}$-$C_{16}$-alkynyl group, a 4-pyranone group, a $C_1$-$C_{16}$-alkylphenyl group, a $C_2$-$C_{16}$-alkenylphenyl group, a $C_2$-$C_{16}$-alkynylphenyl group, a $C_3$-$C_6$-cycloalkyl group, a $C_1$-$C_{16}$-alkyl-$C_3$-$C_6$-cycloalkyl group, a $C_2$-$C_{16}$-alkenyl-$C_3$-$C_6$-cycloalkyl group and a $C_2$-$C_{16}$-alkynyl-$C_3$-$C_6$-cycloalkyl group; each of these groups being optionally substituted with one or more substituent(s) chosen independently of each other as being a hydroxy group, an amine group, a $C_1$-$C_6$-alkyl group, a $C_1$-$C_6$-hydroxyalkyl group, a $C_1$-$C_6$-alkoxy group, a $C_1$-$C_6$-alkylthio group, a $C_1$-$C_6$-alkylcarbonyloxy group, a phenyl group, a $C_1$-$C_6$-alkoxyphenyl group, or a $C_2$-$C_6$-alkenylphenyl group optionally substituted with one or more substituent(s) chosen independently of each other as being a $C_1$-$C_6$-alkyl group, a $C_1$-$C_6$-hydroxyalkyl group, a $C_1$-$C_6$-alkoxy group, a $C_1$-$C_6$-thioalkyl group or a $C_1$-$C_6$-alkylcarbonyloxy group;

$R^5$ and $R^6$ are chosen independently of each other as being a hydrogen atom or a group selected among $C_1$-$C_{16}$-alkyl, $C_2$-$C_{16}$-alkenyl, $C_2$-$C_{16}$-alkynyl, phenyl, $C_1$-$C_{16}$-alkylphenyl, $C_2$-$C_{16}$-alkenylphenyl, $C_2$-$C_{16}$-alkynylphenyl, $C_1$-$C_{16}$-alkoxyindole, $C_3$-$C_6$-cycloalkyl, $C_1$-$C_{16}$-alkyl-$C_3$-$C_6$-cycloalkyl, $C_2$-$C_{16}$-alkenyl-$C_3$-$C_6$-cycloalkyl and $C_2$-$C_{16}$-alkynyl-$C_3$-$C_6$-cycloalkyl; each of these groups being optionally substituted with one or more substituent(s) chosen independently of each other as being a hydroxy group, an amine group, a $C_1$-$C_6$-alkyl group, a $C_1$-$C_6$-hydroxyalkyl group, a $C_1$-$C_6$-alkoxy group, a $C_1$-$C_6$-thioalkyl group, a $C_1$-$C_6$-alkylcarbonyloxy group, a phenyl group, a $C_1$-$C_6$-alkoxyphenyl group, or a $C_2$-$C_6$-alkenylphenyl group optionally substituted with one or more substituent(s) chosen independently of each other as being a $C_1$-$C_6$-alkyl group, a $C_1$-$C_6$-hydroxyalkyl group, a $C_1$-$C_6$-alkoxy group, a $C_1$-$C_6$-thioalkyl group or a $C_1$-$C_6$-alkylcarbonyloxy group;

or, $R^5$ and $R^6$ form, with the nitrogen atom to which they are linked, a heterocycle selected among piperidine, morpholine, hexamethyleneimine or pyrrolidine, optionally substituted with one or more $C_1$-$C_6$-alkyl;

with the exception of the following compounds:
4-acetoxy-3,5-dimethoxy-N-morpholino-cinnamamide;
4-acetoxy-3,5-dimethoxy-N-(2-methylmorpholino)-cinnamamide; and
4-acetoxy-3,5-dimethoxy-N-(3,4,5-trimethoxyphenyl)-cinnamamide.

2. The compound according to claim 1, wherein $R^1$ is chosen as being a —(C=O)—$R^3$ group.

3. The compound according to claim 1, wherein $R^3$ is chosen as being a methyl, an ethyl, a propyl, a butyl, a pentyl or a hexyl group.

4. The compound according to claim 1, wherein $R^4$ is chosen as being a $C_{12}$-$C_{16}$-alkyl group, a phenyl group, a 4-pyranone group, a $C_1$-$C_{16}$-alkylphenyl group, a $C_2$-$C_{16}$-alkenylphenyl group and a $C_3$-$C_6$-cycloalkyl group, each of these groups being optionally substituted with one or more substituent(s) chosen independently of each other as being a hydroxy group, an amine group, a $C_1$-$C_6$-alkyl group, a $C_1$-$C_6$-hydroxyalkyl group, a $C_1$-$C_6$-alkoxy group, a $C_1$-$C_6$-alkylthio group, a $C_1$-$C_6$-alkylcarbonyloxy group, a piperidine group, a morpholine group, a phenyl group, a $C_1$-$C_6$-alkoxyphenyl group, or a $C_2$-$C_6$-alkenylphenyl group optionally substituted with one or more $C_1$-$C_6$-alkylcarbonyloxy.

5. The compound according to claim 4, wherein $R^4$ is chosen as being a $C_{12}$-$C_{16}$-alkyl group, a 4-pyranone group optionally substituted with one or more substituent(s) chosen independently of each other as being a $C_1$-$C_6$-hydroxyalkyl group; a phenyl group optionally substituted with one or more substituent(s) chosen independently of each other as being a $C_1$-$C_6$-alkyl or a $C_1$-$C_6$-hydroxyalkyl group; a $C_1$-$C_{16}$-alkylphenyl group optionally substituted with one or more substituent(s) chosen independently of each other as being a $C_1$-$C_6$-alkoxy group, a $C_1$-$C_6$-alkylthio group, a $C_1$-$C_6$-alkylcarbonyloxy group, a $C_1$-$C_6$-alkoxyphenyl group or a $C_2$-$C_6$-alkenylphenyl group which is in turn substituted with one or more $C_1$-$C_6$-alkylcarbonyloxy, $C_2$-$C_{16}$-alkenylphenyl; and $C_3$-$C_6$-cycloalkyl.

6. The compound according to claim 5, wherein $R^4$ is chosen as being the 4-pyranone, the 3,4,5-trimethoxy benzyl or a $C_{16}$-alkyl.

7. The compound according to claim 1, wherein $R^5$ and $R^6$ are chosen independently of each other as being a hydrogen atom or a group selected among $C_1$-$C_{16}$-alkyl, $C_2$-$C_{16}$-alkenyl, phenyl, piperidine, morpholine, $C_1$-$C_{16}$-alkylphenyl, $C_1$-$C_{16}$-alkoxyindole and $C_3$-$C_6$-cycloalkyl, each of these groups being optionally substituted with one or more substituent(s) chosen independently of each other as being a hydroxy group, an amine group, a $C_1$-$C_6$-alkyl group, a $C_1$-$C_6$-hydroxyalkyl group, a $C_1$-$C_6$-alkoxy group, a $C_1$-$C_6$-thioalkyl group, a $C_1$-$C_6$-alkylcarbonyloxy group, a phenyl group, a $C_1$-$C_6$-alkoxyphenyl group, or a $C_2$-$C_6$-alkenylphenyl group optionally substituted with one or more substituent(s) chosen independently of each other as being a $C_1$-$C_6$-alkyl group, a $C_1$-$C_6$-hydroxyalkyl group, a $C_1$-$C_6$-alkoxy group, a $C_1$-$C_6$-thioalkyl group or a $C_1$-$C_6$-alkylcarbonyloxy group.

8. The compound according to claim 7, wherein $R^5$ and $R^6$ are chosen independently of each other as being a hydrogen atom or a group selected among $C_1$-$C_{16}$-alkyl; $C_2$-$C_{16}$-alkenyl; phenyl; piperidine; morpholine optionally substituted with one or more substituent(s) chosen independently of each other as being a hydroxy or a $C_1$-$C_6$-alkyl group; a $C_1$-$C_{16}$-alkylphenyl group optionally substituted with one or more substituent(s) chosen independently of each other as being a hydroxy or a $C_1$-$C_6$-alkoxy group, a $C_1$-$C_{16}$-alkoxyindole group; and a $C_3$-$C_6$-cycloalkyl group.

9. The compound according to claim 8, wherein $R^5$ is a hydrogen atom and $R^6$ is chosen as being a $C_{16}$-alkyl group or the 4-hydroxyphenylethyl.

10. A cosmetic composition comprising a compound according to claim 1.

11. The composition according to claim 10 for cosmetic treatment of skin ageing, for a slimming cosmetic treatment and/or for a skin-whitening cosmetic treatment.

12. A pharmaceutical composition comprising a compound according to claim 1.

13. The composition according to claim 12 for use in the context of treatment of Hutchinson-Gilford disease.

* * * * *